United States Patent
Wu et al.

(10) Patent No.: US 10,456,791 B2
(45) Date of Patent: Oct. 29, 2019

(54) METHOD AND APPARATUS FOR PERFORMING CONTACTLESS OPTICALLY-INDUCED DIELECTROPHORESIS FOR SEPARATION OF CIRCULATING TUMOR CELLS

(71) Applicant: Chang Gung University, Taoyuan (TW)

(72) Inventors: Min-Hsien Wu, Kaohsiung (TW); Chia-Hsun Hsieh, New Taipei (TW); Hung-Ming Wang, Taipei (TW); Wen-Pin Chou, Taipei (TW); Tzu-Keng Chiu, New Taipei (TW)

(73) Assignee: Ace Medical Technology Co., Ltd., Taipei (TW)

( * ) Notice: Subject to any disclaimer, the term of this patent is extended or adjusted under 35 U.S.C. 154(b) by 239 days.

(21) Appl. No.: 15/366,593

(22) Filed: Dec. 1, 2016

(65) Prior Publication Data
US 2017/0297036 A1    Oct. 19, 2017

(30) Foreign Application Priority Data
Apr. 19, 2016  (TW) .............................. 105112116 A

(51) Int. Cl.
*B03C 5/00* (2006.01)
*B01L 3/00* (2006.01)
(Continued)

(52) U.S. Cl.
CPC ........ *B03C 5/005* (2013.01); *B01L 3/502761* (2013.01); *B03C 5/026* (2013.01); *C12N 13/00* (2013.01); *B01L 2200/027* (2013.01); *B01L 2200/0647* (2013.01); *B01L 2200/0652* (2013.01); *B01L 2200/0668* (2013.01);
(Continued)

(58) Field of Classification Search
None
See application file for complete search history.

(56) References Cited

U.S. PATENT DOCUMENTS

| 2010/0216208 A1* | 8/2010 | Mueth ................... G02B 21/32 |
| | | 435/173.9 |
| 2016/0040232 A1* | 2/2016 | Lin .......................... A61M 1/36 |
| | | 506/9 |

FOREIGN PATENT DOCUMENTS

TW          201502503 A          1/2015

OTHER PUBLICATIONS

Taiwan Intellectual Property Office, Notice of Allowance for Taiwan Application No. 105112116, dated Jan. 5, 2018, 2 pages and 2 pages of English Translation.
(Continued)

*Primary Examiner* — Erik B Crawford

(57) ABSTRACT

A method for performing contactless ODEP for separation of CTCs is provided with the steps of obtaining patients' blood with rare cell suspected CTCs; adding at least one fluorescent antibody binding to CTCs into the blood; staining the blood; injecting the stained blood with fluorescent dye into an ODEP device and then performing fluorescent image identification; trapping the CTCs with at least one fluorescent antibody in the ODEP device by creating an image pattern and then generating an ODEP force; Separating the trapped CTCs from other non-CTCs cells; absorbing the trapped CTCs; and obtaining a high purity of CTCs. An apparatus for performing contactless ODEP for separation of CTCs is also provided.

2 Claims, 7 Drawing Sheets

(51) Int. Cl.
*C12N 13/00* (2006.01)
*B03C 5/02* (2006.01)
*G01N 15/10* (2006.01)
*G01N 1/40* (2006.01)
*G01N 15/14* (2006.01)

(52) U.S. Cl.
CPC .................. *B01L 2300/0816* (2013.01); *B01L 2400/0424* (2013.01); *B03C 2201/26* (2013.01); *G01N 2001/4038* (2013.01); *G01N 2015/1081* (2013.01); *G01N 2015/149* (2013.01)

(56) References Cited

OTHER PUBLICATIONS

Taiwan Intellectual Property Office, Second Official Action for Taiwan Application No. 105112116, dated Jan. 24, 2017, 5 pages and 5 pages of English Translation.
Taiwan Intellectual Property Office, First Official Action for Taiwan Application No. 105112116, dated Aug. 31, 2016, 5 pages and 3 pages of English Translation.
Commitment International Patent & Trademark Office, Certificate for Taiwan Application No. 105112116, dated Mar. 2, 2018, 3 pages.

* cited by examiner

METHOD AND APPARATUS FOR PERFORMING CONTACTLESS OPTICALLY-INDUCED DIELECTROPHORESIS FOR SEPARATION OF CIRCULATING TUMOR CELLS

BACKGROUND OF THE INVENTION

1. Field of the Invention

The invention relates to methods and apparatuses for separation of circulating tumor cells (CTCs) and more particularly to a method and apparatus for performing contactless optically-induced dielectrophoresis (ODEP) for the separation of CTCs in which an initial cells separation is done using a conventional reagent separation technique, micro fluid and ODEP are employed, and images of fluorescent antibody are used to select and separate the CTCs from the target cells. 100% purity of CTCs can be obtained for subsequent gene analysis.

2. Description of Related Art

Methods for the separation of CTCs from the blood are well known in the art. For example, Ficoll solution is used to separating red blood cells (RBCs) from the blood, magnetic beads of antibody are used to capture white blood cells (WBCs), micro fluid electrodes are used by a chemical or physical method to separate blood cells from the blood, etc.

However, purity of the obtained CTCs is less than 100%. That means only tens to hundreds CTCs are available for high precision sub-generation gene order analysis and they may be seriously interfered by other blood cells. As a result, the gene order analysis is not correct and unacceptable.

Thus, the need for improvement still exists.

SUMMARY OF THE INVENTION

It is therefore one object of the invention to provide a method for performing contactless optically-induced dielectrophoresis (ODEP) for separation of circulating tumor cells (CTCs), the method comprising the steps of obtaining patients' blood with rare cell suspected CTCs; adding at least one fluorescent antibody binding to CTCs into the blood; staining the blood; injecting the stained blood with fluorescent dye into an ODEP device and then performing fluorescent image identification; trapping the CTCs with at least one fluorescent antibody in the ODEP device by creating an image pattern and then generating an ODEP force; Separating the trapped CTCs from other non-CTCs cells; absorbing the trapped CTCs; and obtaining a high purity of CTCs.

It is another object of the invention to provide an apparatus for performing contactless optically-induced dielectrophoresis for separation of circulating tumor cells for the implementation of the method, the apparatus comprising an ODEP device including a first conductive glass, a bio-compatible membrane, and a second conductive glass wherein the bio-compatible membrane is disposed below the first conductive glass, the bio-compatible membrane includes a transverse main channel and a longitudinal micro channel perpendicular to the main channel and joining the main channel at a cell separation zone; the first conductive glass includes a first hole and a second hole aligned with two ends of the main channel respectively, and a third hole aligned with one end of the micro channel; and the second conductive glass is disposed below the bio-compatible membrane; a sample receiving member disposed on and aligned with the first hole; an exhaust discharge member disposed on and aligned with the second hole; a target collection member disposed on and aligned with the third hole; and a controller including an optical projection device and an image fetch device.

It is a further object of the invention to provide an apparatus for performing contactless optically-induced dielectrophoresis for separation of circulating tumor cells for the implementation of the method, the apparatus comprising an ODEP device including a first conductive glass and a second conductive glass wherein the first conductive glass is disposed on the second conductive glass; the first conductive glass includes a transverse main channel and a longitudinal micro channel perpendicular to the main channel and joining the main channel at a cell separation zone; and the first conductive glass includes a first hole and a second hole aligned with two ends of the main channel respectively, and a third hole aligned with one end of the micro channel; a sample receiving member disposed on and aligned with the first hole; an exhaust discharge member disposed on and aligned with the second hole; a target collection member disposed on and aligned with the third hole; and a controller including an optical projection device and an image fetch device.

The invention has the following advantages and benefits in comparison with the conventional art: CTCs sample having a 100% purity is made possible. Required fluorescent antibody of CTCs can be marked for analysis as long as the fluorescent mark can be identified by an imaging system. Target cells can be obtained. White blood cells (WBCs) of a cancer patient, cancer stem cells in the CTCs, and CTCs of high transfer having surface antigens can be marked by the fluorescent antibody of CTCs for medical search. A method for precise separation of CTCs is made possible. The separated CTCs from a cancer patient can be used to replace high risk samples obtained from cancer cells of a cancer patient. Cancer cells gene analysis is made easy since effective samples can be safely obtained from a cancer patient. Healed condition of a cancer patient can be determined correctly. The high purity CTCs are not affected by healthy cells and thus a next generation sequencing (NGS) can be performed on CTCs of a cancer patient. Medical effects of anti-cancer medicine administered to a cancer patient can be well observed. Medicine companies can use the invention for new drug development. Precision and effectiveness of CTCs gene analysis are greatly increased.

The above and other objects, features and advantages of the invention will become apparent from the following detailed description taken with the accompanying drawings.

DETAILED DESCRIPTION OF THE INVENTION

Optically-induced dielectrophoresis (ODEP) of the invention employs light as a virtual electrode. In detail, light impinges on light guide materials of two tablet electrodes respectively. Uneven electric fields are generated around optical patterns. Polarized particles can be manipulated by the uneven electric fields. In an operation, an individual may operate a personal computer to direct light projected from a projector to the particles for manipulation purposes.

Figure 1:
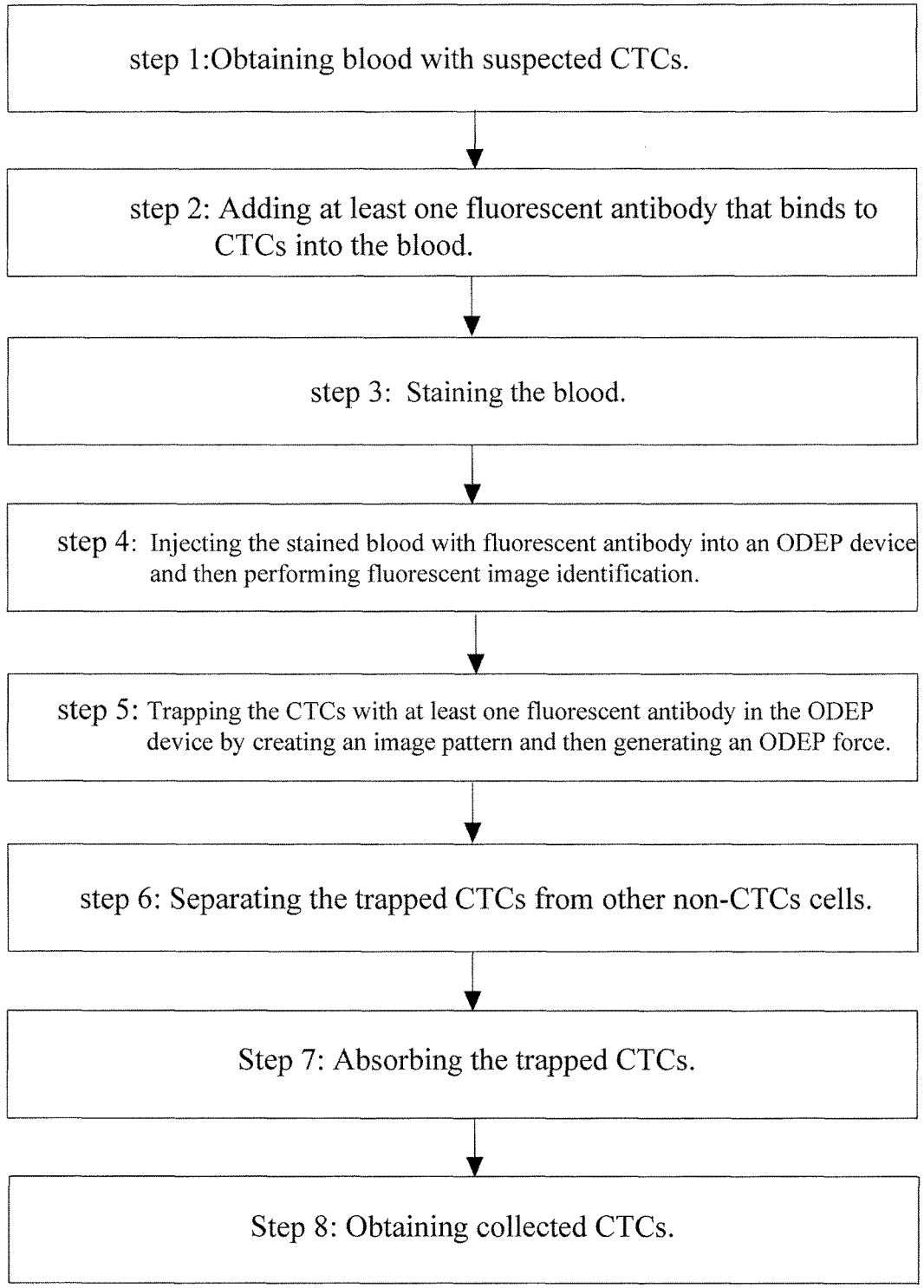
FIG. 1 is a flow chart of a method for performing contactless optically-induced dielectrophoresis for separation of circulating tumor cells according to the invention.

Referring to FIG. 1, a method for performing contactless optically-induced dielectrophoresis (ODEP) for separation of circulating tumor cells (CTCs) in accordance with the invention is illustrated. The method comprises the following steps as discussed in detail below.

Step 1: Obtaining blood with rare cell suspected CTCs.

Step 2: Adding at least one fluorescent antibody binding to CTCs into the blood.

Step 3: Staining the blood.

Step 4: Injecting the stained blood with fluorescent dye into an ODEP device and then performing fluorescent image identification.

Step 5: Trapping the CTCs with at least one fluorescent antibody in the ODEP device by creating an image pattern and then generating an ODEP force.

Step 6: Separating the trapped CTCs from other non-CTCs cells.

Step 7: Absorbing the trapped CTCs.

Step 8: Obtaining a high purity of CTCs after repeating steps 5 and 6.

The red blood cells (RBCs) and the white blood cells (WBCs) can be removed from the obtained blood between step 1 and step 2. Such RBCs and WBCs removal step can increase CTCs collection speed after blood being stained. The removal of the RBCs can be done by a physical separation method or a chemical removal method. The removal of the WBCs can be done by the group identification of CD45 cocktail magnetic antibody. Also, the WBCs having the expression of CD45 can be removed in cell nuclei.

Before the absorption of the trapped CTCs in step 7, the purity of the trapped CTCs can be identified again by observing the fluorescent images. The purpose of such identification is to determine whether the non-target cells having fluorescent expression are there. If yes, the non-target cells are identified by the fluorescent images in order to determine whether they have cell nuclei and determine whether they are pseudo positive target cells. Thus It can further increase the purity of the trapped CTCs.

The physical method of removing RBCs from the blood comprises the following steps of (a) adding a material capable of separating cells having a high density from cells having a low density to a test tube, and adding blood to the test tube to obtain a solution in which volumetric ratio of the material to the blood is 3:4; (b) rotating the test tube at a centrifugal speed of 400 rpm for 30 minutes to convert the solution in the test tube into an upper portion of serum, an intermediate portion of transparent product, and a lower portion of RBCs; (c) removing blood having a single cell nucleus at a milky white interface between the upper portion of serum and the intermediate portion of transparent product from the test tube and adding same to another test tube; (d) using saline to wash the blood for a predetermined number of times; and (e) obtaining blood without RBCs.

Preferably, the material is either sugar or polysaccharide.

The chemical method of removing RBCs from the blood employs osmoses to explode RBCs of the blood without cell nuclei in order to obtain WBCs having cell nuclei. The chemical method comprises the following steps of (a) preparing a reagent 1×RBC lysis buffer 1,000 ml in a test tube by mixing 8.26 g of $NH_4Cl$, 1.19 g of $NaHCO_3$, 200 μL 0.5 M pH8 of EDTA, and 1,000 ml of distilled water without microorganisms until the reagent has pH7.3; (b) adding blood to the reagent in which volumetric ratio of the blood to the reagent is 1:5, and reacting for 10 minutes; (c) rotating the test tube at a centrifugal speed of 400 rpm for 5 minutes to remove the upper portion of serum; (d) using 10 ml of PBS to wash the blood cells once and rotating the test tube at a centrifugal speed of 400 rpm for 5 minutes to remove the upper portion of serum; and (e) obtaining WBCs and CTCs having cell nuclei from the remains of the test tube.

In step 2, the fluorescent antibody is a unique antibody for binding to the CTCs. The fluorescent antibody can collect and combine those suspected tumor cells having a weak CD45 expression or none CD45 expression. The unique antibody for binding to the CTCs is comprised of adhesion protein of epithelium, keratin protein of cells, surface antigens of cancer stem cell, epidermal growth factor receptor, and adhesion protein of calcium.

The high purity of CTCs are used to detect cancer and heal wounds after surgery. Further, the high purity CTCs are used to analyze gene, test resistance of medicine, and test medicine.

Figure 2:
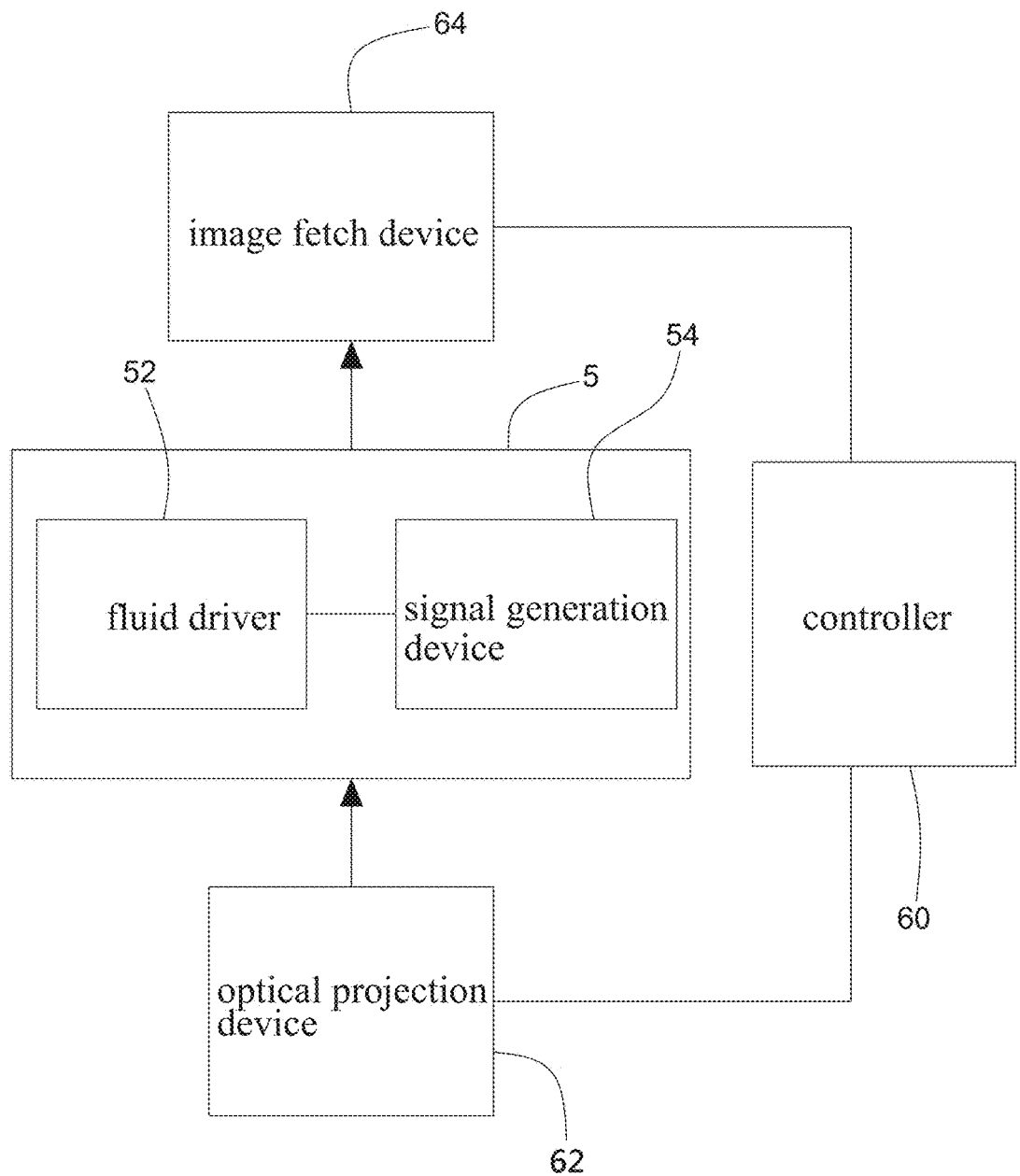
FIG. 2 is a block diagram of an apparatus for performing contactless optically-induced dielectrophoresis for separation of circulating tumor cells according to the invention.
Figure 3:
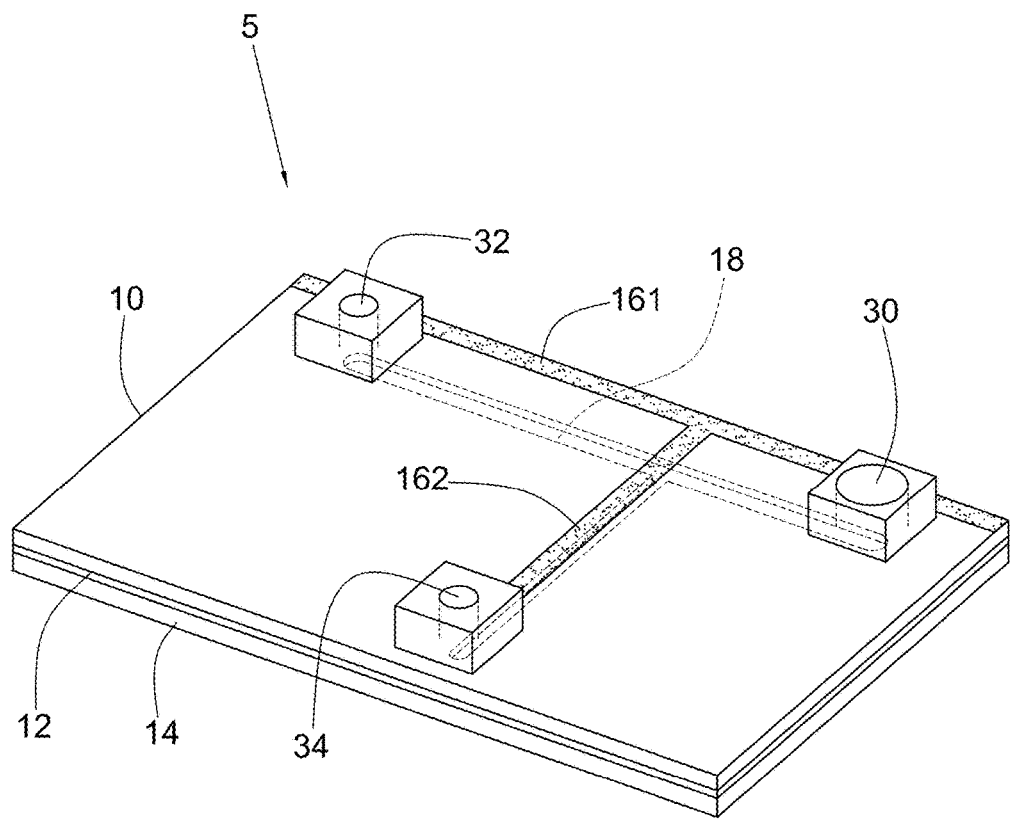
FIG. 3 is a perspective view of the ODEP device of a first preferred embodiment.
Figure 4:
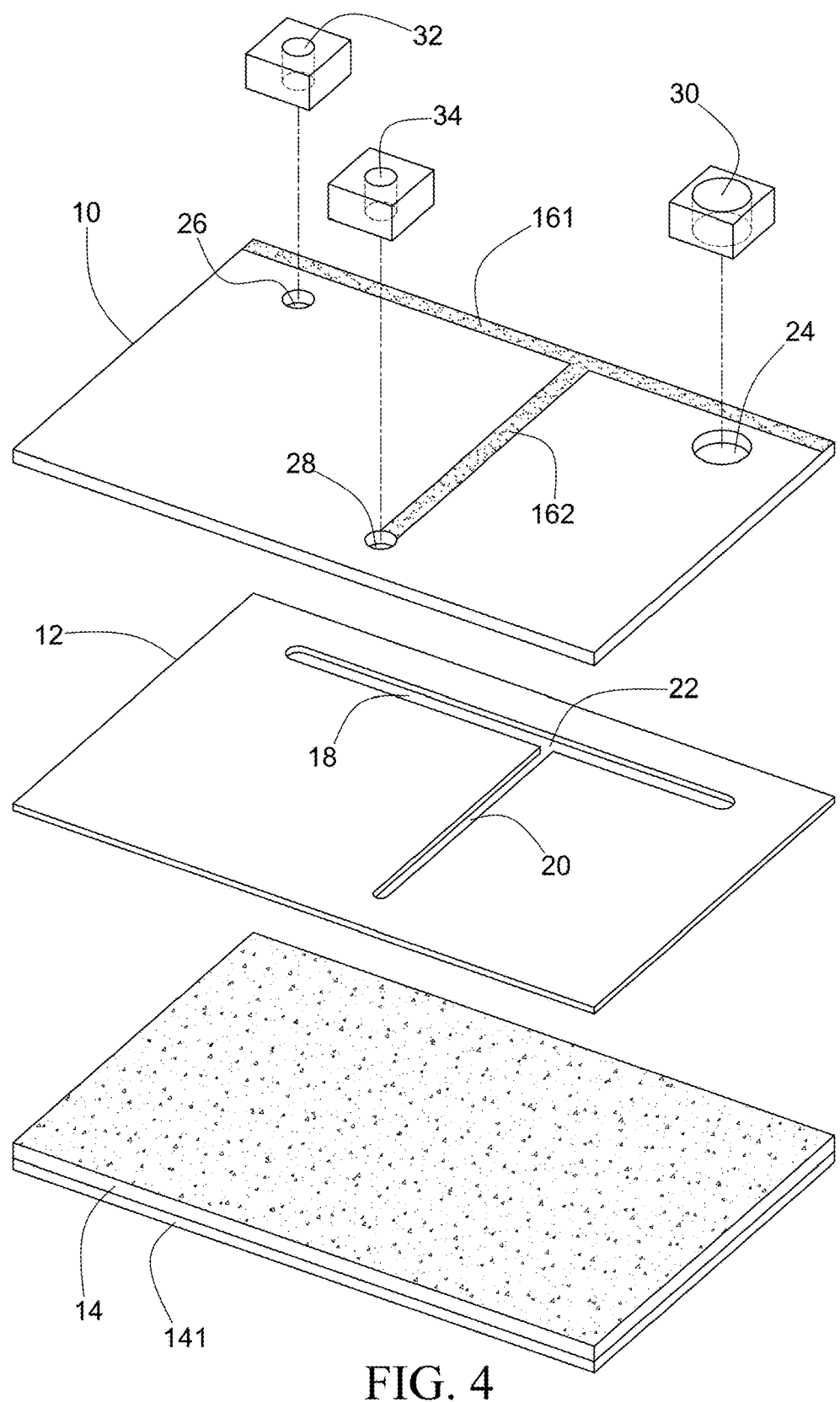
FIG. 4 is an exploded view of the ODEP device shown in FIG. 3.

Referring to FIGS. 2 to 4, an apparatus for performing contactless optically-induced dielectrophoresis for separation of circulating tumor cells in accordance with a first preferred embodiment of the invention comprises an ODEP device 5, a first conductive glass 10, a bio-compatible membrane 12, and a second conductive glass 14. The bio-compatible membrane 12 is disposed below the first conductive glass 10. A transverse main channel 18 is provided on the bio-compatible membrane 12. A longitudinal micro channel 20 is provided on the bio-compatible membrane 12, is perpendicular to the main channel 18, and joins the main channel 18 at a cell separation zone 22 in the intermediate portion of the main channel 18. A first hole 24 and a second hole 26 are formed through the first conductive glass 10 and aligned with two ends of the main channel 18 respectively. A third hole 28 is formed through the first conductive glass 10 and aligned with one end of the micro channel 20. A sample receiving member 30 is provided on and aligned with the first hole 24. An exhaust discharge member 32 is provided on and aligned with the second hole 26. A target collection member 34 is provided on and aligned with the third hole 28. The second conductive glass 14 is provided below the bio-compatible membrane 12. A controller 60 includes an optical projection device 62 and an image fetch device 64.

A first electrode channel 161 is provided along an edge of the first conductive glass 10 and corresponds to the main channel 18. A second electrode channel 162 is provided to be perpendicular to the first electrode channel 161 and joins the first electrode channel 161. The second electrode channel 162 corresponds to the micro channel 20.

The second conductive glass 14 includes a light guide layer 141 formed on a bottom. The light guide layer 141 is distal the first conductive glass 10. The light guide layer 14 is configured to guide light.

The ODEP device 5 includes a fluid driver 52 and a signal generation device 54 connected to the fluid driver 52.

Figure 5:
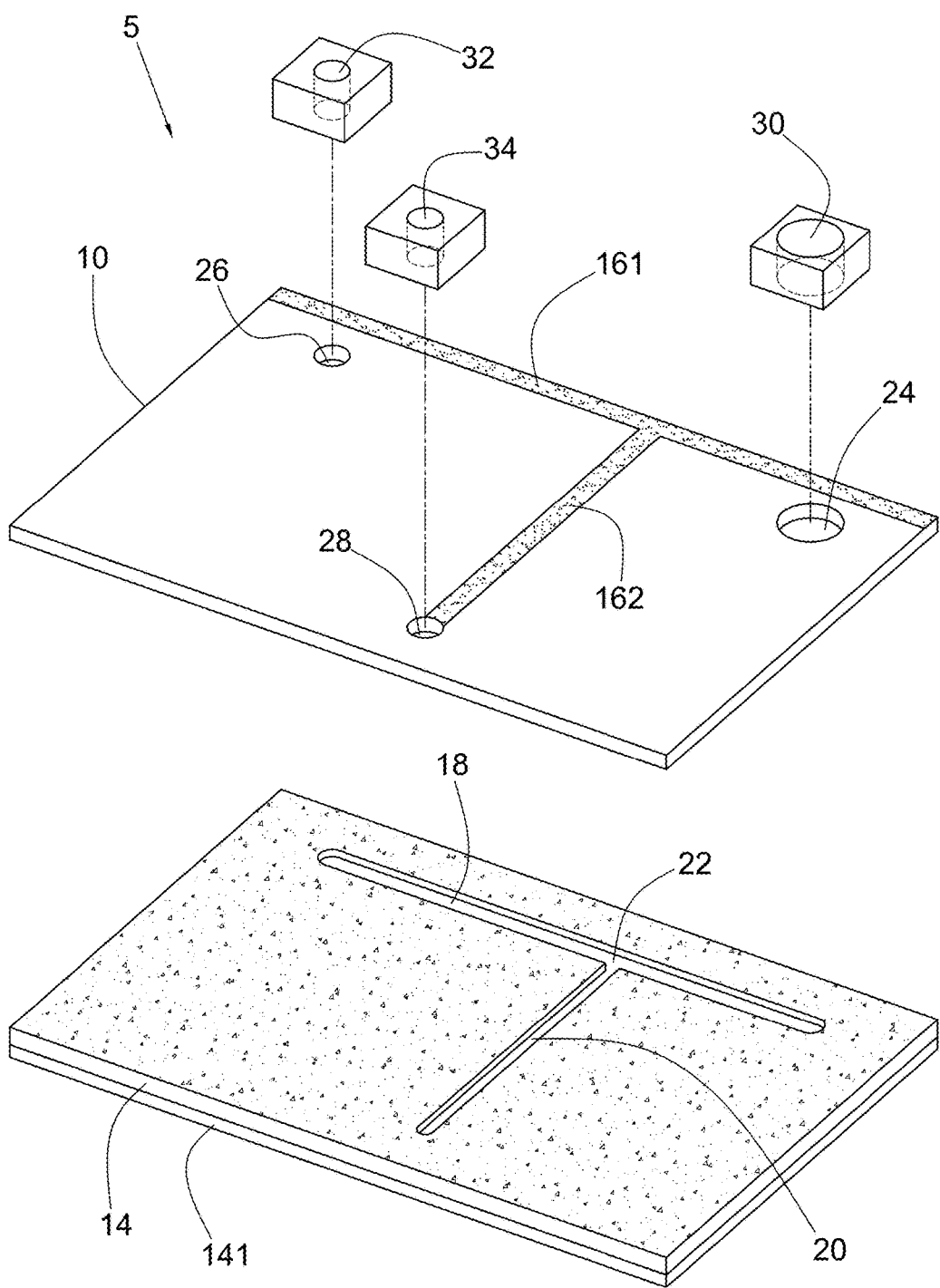
FIG. 5 is an exploded view of an ODEP device of a second preferred embodiment.
Figure 6:
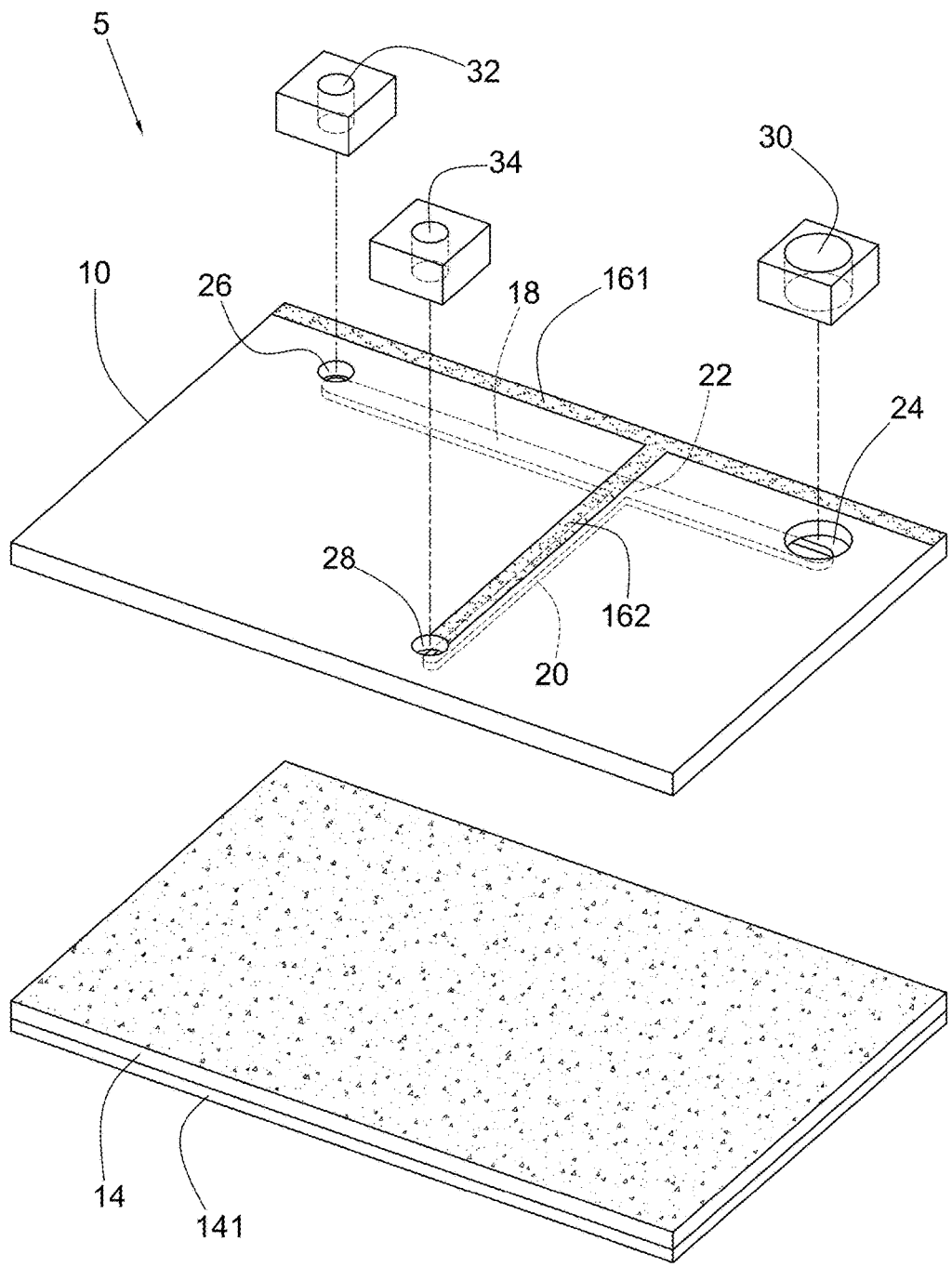
FIG. 6 is an exploded view of an ODEP device of a third preferred embodiment.

Referring to FIGS. 2, 5 and 6, an apparatus for performing contactless optically-induced dielectrophoresis for separation of circulating tumor cells in accordance with a second preferred embodiment of the invention comprises an ODEP device 5, a first conductive glass 10, and a second conductive glass 14. The first conductive glass 10 is provided on the second conductive glass 14. A transverse main channel 18 is provided on the first conductive glass 14. A longitudinal micro channel 20 is provided on the first conductive glass 14, is perpendicular to the main channel 18, and joins the main channel 18 at a cell separation zone 22 in the intermediate portion of the main channel 18. A first hole 24 and a second hole 26 are formed through the first conductive glass 10 and aligned with two ends of the main channel 18 respectively. A third hole 28 is formed through the first conductive glass 10 and aligned with one end of the micro channel 20. A sample receiving member 30 is provided on and aligned with the first hole 24. An exhaust discharge member 32 is provided on and aligned with the second hole 26. A target collection member 34 is provided on and aligned with the third hole 28. A controller 60 includes an optical projection device 62 and an image fetch device 64.

A first electrode channel 161 is provided along an edge of the first conductive glass 10 and corresponds to the main channel 18. A second electrode channel 162 is provided to be perpendicular to the first electrode channel 161 and joins the first electrode channel 161. The second electrode channel 162 corresponds to the micro channel 20.

The second conductive glass 14 includes a light guide layer 141 formed on a bottom. The light guide layer 141 is distal the first conductive glass 10.

The ODEP device 5 includes a fluid driver 52 and a signal generation device 54 connected to the fluid driver 52.

In operation, both the first and second electrode channels 161 and 162 are positive and the second conductive glass 14 is negative if the first conductive glass 10 is positive. To the contrary, the second conductive glass 14 is positive if the first conductive glass 10 is negative.

Figure 7:
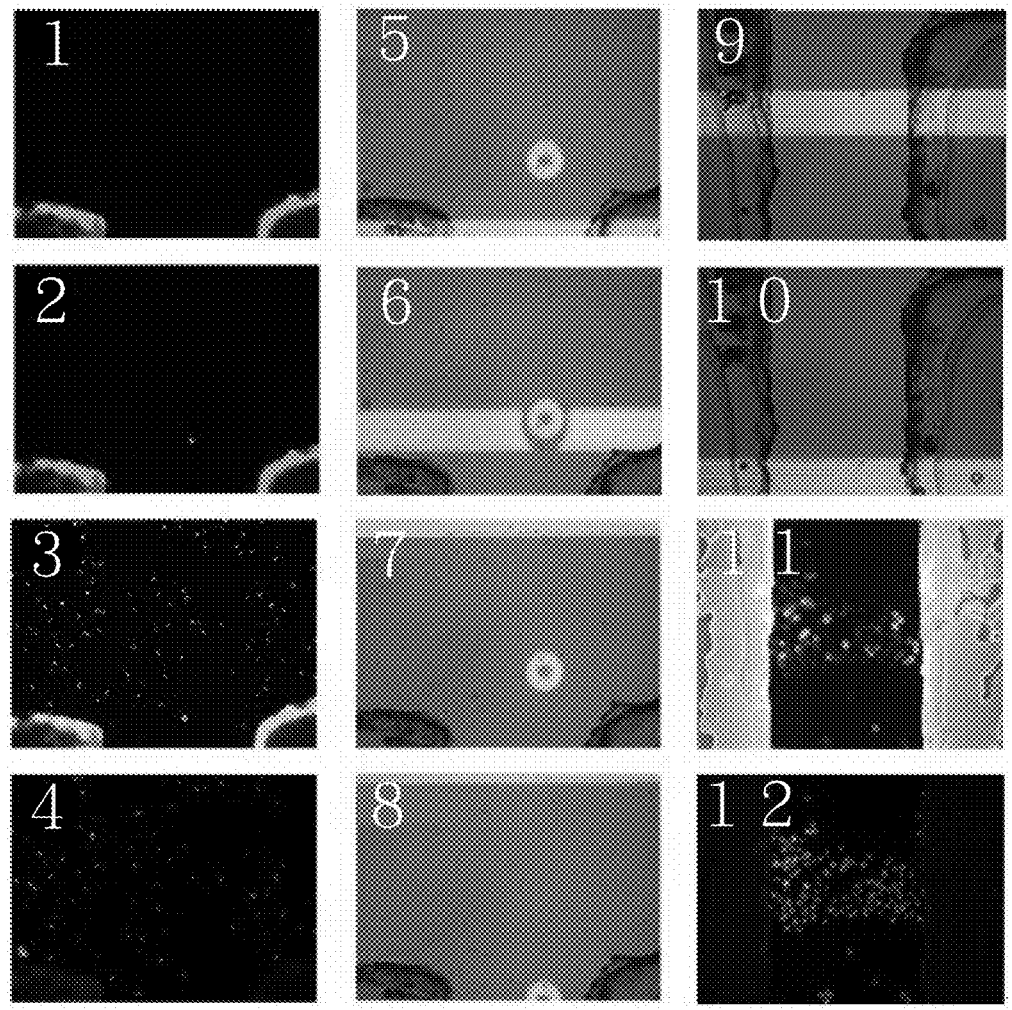
FIG. 7 illustrates scanning electron microscopy images of the separation of circulating tumor cells according to the invention.

Referring to FIG. 7, details of the flow chart of FIG. 1 are discussed below. Blood sample is obtained from a cancer patient. RBCs and WBCs are removed from the blood sample using a conventional method. The remaining blood sample is dyed with commercially available fluorescent antibody. The dyed blood sample it added to a sample receiving member. Fluorescent image identification is performed on the dyed blood sample to track fluorescent target CTCs of the flowing blood cells suspension fluid. In response to appearing of the fluorescent target CTCs on the cell separation zone, the blood cells suspension fluid is stopped flowing. The blood cells suspension fluid begins to flow again after collecting the CTCs. Target CTCs and non-target CTCs (e.g., WBCs) are identified. It is to determine the target CTCs have nuclei and they are not pseudo positive fluorescent target cells or doped target CTCs. ODEP is performed to select target CTCs. ODEP is performed to remove the non-target CTCs (e.g., WBCs) from the selected target CTCs and place it in a target collection member. The target CTCs are collected in the target collection member. ODEP is performed to collect the target CTCs in a next stage. Fluorescent images 1 to 12 are used to identify purity of the CTCs and determine whether the CTCs have nuclei not pseudo positive target cells. Finally, the CTCs are absorbed for subsequent analysis.

The operation time is 20 minutes in which 2.5 ul/min flowing speed is carried out in the first ten minutes and a stop is carried out in the next ten minutes. Cell size is 30 ul. The number of cells is $10^4$.

The invention has the following advantages and benefits in comparison with the conventional art: CTCs sample having a 100% purity is made possible. Required fluorescent antibody of CTCs can be marked for analysis as long as the fluorescent mark can be identified by an imaging system. Target cells can be obtained. White blood cells (WBCs) of a cancer patient, cancer stem cells in the CTCs, and CTCs of high transfer having surface antigens can be marked by the fluorescent antibody of CTCs for medical search. A method for precise separation of CTCs is made possible. The separated CTCs from a cancer patient can be used to replace high risk samples obtained from cancer cells of a cancer patient. Cancer cells gene analysis is made easy since effective samples can be safely obtained from a cancer patient. Healed condition of a cancer patient can be determined correctly. The high purity CTCs are not affected by healthy cells and thus a next generation sequencing (NGS) can be performed on CTCs of a cancer patient. Medical effects of anti-cancer medicine administered to a cancer patient can be well observed. Medicine companies can use the invention for new drug development. Precision and effectiveness of CTCs gene analysis are greatly increased.

While the invention has been described in terms of preferred embodiments, those skilled in the art will recognize that the invention can be practiced with modifications within the spirit and scope of the appended claims.

What is claimed is:

1. A method for performing contactless optically-induced dielectrophoresis (ODEP) for separation of circulating tumor cells (CTCs), the method comprising the steps of:
   (1) obtaining blood with suspected CTCs;
   (2) adding at least one fluorescent antibody that binds to the CTCs into the blood to form stained blood;
   (3) injecting the stained blood with the at least one fluorescent antibody into a sample receiving member of an ODEP device wherein the ODEP device includes a first conductive glass and a second conductive glass, the first conductive glass includes a transverse main channel and a longitudinal micro channel joining the main channel at a cell separation zone, and the first conductive glass includes a first hole and a second hole aligned with two ends of the main channel respectively, a third hole aligned with one end of the microchannel that is distal to the cell separation zone, the sample receiving member disposed on and aligned with the first hole, an exhaust discharge member disposed on and aligned with the second hole, a target collection member disposed on and aligned with the third hole, and a controller including an optical projection device and an image fetch device;
   (4) performing fluorescent image identification by immunofluorescent microscopic observation using the optical projection device and the image fetch device to identify and distinguish the CTCs bound to the at least one fluorescent antibody from pseudo positive target cells that have fluorescent expression and lack cell nuclei;
   (5) trapping the identified CTCs bound to the at least one fluorescent antibody in the ODEP device by creating an image pattern by projecting a light image and then generating an ODEP force;
   (6) separating the trapped CTCs from other non-CTCs at the cell separation zone;

(7) collecting the trapped CTCs in the target collection member; and
(8) obtaining the collected CTCs from the target collection member.

2. The method of claim 1, wherein red blood cells (RBCs) and white blood cells (WBCs) are removed from the blood between step (1) and step (2).

* * * * *